(12) United States Patent
Kenmoku et al.

(10) Patent No.: US 6,869,782 B2
(45) Date of Patent: Mar. 22, 2005

(54) POLYHYDROXYALKANOATE THAT COMPRISES UNIT HAVING (METHYLSULFANYL) PHENOXY STRUCTURE IN SIDE CHAIN THEREOF AND PROCESS FOR PRODUCING THE SAME

(75) Inventors: Takashi Kenmoku, Kanagawa (JP); Etsuko Sugawa, Kanagawa (JP); Tetsuya Yano, Kanagawa (JP); Takeshi Imamura, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 320 days.

(21) Appl. No.: 10/187,808

(22) Filed: Jul. 3, 2002

(65) Prior Publication Data

US 2003/0109015 A1 Jun. 12, 2003

(30) Foreign Application Priority Data

Jul. 10, 2001 (JP) .................................... 2001-208705

(51) Int. Cl.[7] .......................... C08G 63/02; C08G 79/00
(52) U.S. Cl. ...................... 435/130; 528/272; 528/274; 528/294; 528/295; 528/360
(58) Field of Search .......................... 435/130; 528/272, 528/274, 294, 295, 360

(56) References Cited

U.S. PATENT DOCUMENTS

| | | | |
|---|---|---|---|
| 4,393,167 A | 7/1983 | Holmes et al. | 525/64 |
| 4,876,331 A | 10/1989 | Doi | 528/361 |
| 5,135,859 A | 8/1992 | Witholt et al. | 435/135 |
| 5,200,332 A | 4/1993 | Yamane et al. | 435/135 |
| 5,292,860 A | 3/1994 | Shiotani et al. | 528/361 |
| 5,334,698 A | 8/1994 | Witholt et al. | 528/354 |
| 6,479,621 B2 * | 11/2002 | Honma et al. | 528/361 |
| 6,495,152 B2 * | 12/2002 | Steinbuchel et al. | 424/405 |
| 6,521,429 B2 * | 2/2003 | Honma et al. | 435/135 |
| 6,635,782 B2 * | 10/2003 | Honma et al. | 560/53 |
| 6,645,743 B1 * | 11/2003 | Honma et al. | 435/146 |
| 6,686,439 B2 * | 2/2004 | Kenmoku et al. | 528/272 |
| 2002/0022253 A1 | 2/2002 | Honma et al. | 435/135 |

FOREIGN PATENT DOCUMENTS

| | | |
|---|---|---|
| EP | 1 340 776 | 9/2003 |
| JP | 5-7492 | 1/1993 |
| JP | 5-93049 | 4/1993 |
| JP | 6-15604 | 3/1994 |
| JP | 7-14352 | 2/1995 |
| JP | 7-265065 | 10/1995 |
| JP | 8-19227 | 2/1996 |
| JP | 2642937 | 5/1997 |
| JP | 9-191893 | 7/1997 |
| JP | 2989175 | 10/1999 |
| JP | 2002-80571 | 3/2002 |

OTHER PUBLICATIONS

Katharina Fritzsche et al., "An Unusual Bacterial Polyester with a Phenyl Pendant Group," 191 *Makromol. Chem.* 1957–1965 (1990).

Helmut Ritter et al., "Bacterial Production of Polyesters Bearing Phenoxy Groups in the Side Chains, 1 Poly(3–hydroxy–5–phenoxypentanoate–co–3–hydroxy–9–phenoxy–nonanoate) from *Pseudomonas oleovorans*," 195 *Macromol. Chem. Phys.* 1665–1672 (1994).

Ohyoung Kim et al., "Bioengineering of Poly(β–hydroxyalkanoates) for Advanced Material Applications: Incorporation of Cyano and Nitrophenoxy Side Chain Substituents," 41 (Supp. 1) *Can. J. Microbiol*, 32–43 (1995).

H. Abe, et al., "Biosynthesis from Gluconate of a random copolyester consisting of 3–hydroxy–butyrate and medium–chain–length 3–hydroxyalkanoates by *Pseudomonas* sp. 61–3", Int. J. Biol. Macromol., vol. 16, No. 1, pp. 115 to 119 (1994).

Y. Kim, et al., "Poly–3–hydroxyalkanoates Produced from *Pseudomonas oleovorans* Grown with ω–Phenoxyalkanoates", Macromolecules, vol. 29, pp. 3432 to 3435 (1996).

O. Kim, et al., "Bioengineering of poly(β–hydroxyalkanoates) for advanced material applications: incorporation of cyano and nitrophenoxy side chain substituents", Can. J. Microbiol, vol. 41 (Suppl. 1), pp. 32 to 42 (1995).

H. Ritter, et al., "Bacterial production of polyesters bearing phenoxy groups in the side chains, 1", Macromolecular Chemistry and Physics, vol. 195, pp. 1665 to 1672 (1994).

(List continued on next page.)

*Primary Examiner*—Herbert J. Lilling
(74) *Attorney, Agent, or Firm*—Fitzpatrick, Cella, Harper and Scinto

(57) ABSTRACT

A polyhydroxyalkanoate that comprises a unit represented by the following chemical formula (1):

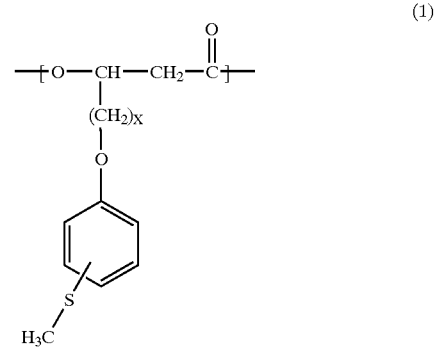

X = 1–8 wherein x is an integer of 1 to 8 being the same or different in the polyhydroxyalkanoate. The microbial production process is also disclosed.

29 Claims, 1 Drawing Sheet

OTHER PUBLICATIONS

Y. Takagi, et al., "Biosynthesis of Polyhydroxyalkanoate with a Thiophenoxy Side Group Obtained from *Pseudomonas putida*," Macromolecules, vol. 32, pp. 8315 to 8318 (1999).

YoungBaek Kim et al., "Poly–3–hydroxyalkanoates Produced from *Pseudomonas oleovorans* Grown with ω–Polyhydroxyalkanoates," 29 *Macromol.* 3432–3435 (1996).

Y.B. Kim et al., "Preparation and Characterization of Poly(β–hydroxyalkanoates) Obtain d from *Pseudomonas oleovorans* Grown with Mixtures of 5–Phenylvaleric Acid and n–Alkanoic Acids," 24 *Macromol.* 5256–5260 (1991).

Safwat Antoun et al., "Production of Chiral Polyester by *Pseudomonas oleovorans* Grown with 5–Phenyl–2,4–Pentadienoic Acid," 3 *Chirality* 492–494 (1991).

"Biodegradable Plastic Handbook", Biodegradable Plastics Society Ed., NTS, pp 178 to197 (1995).

* cited by examiner

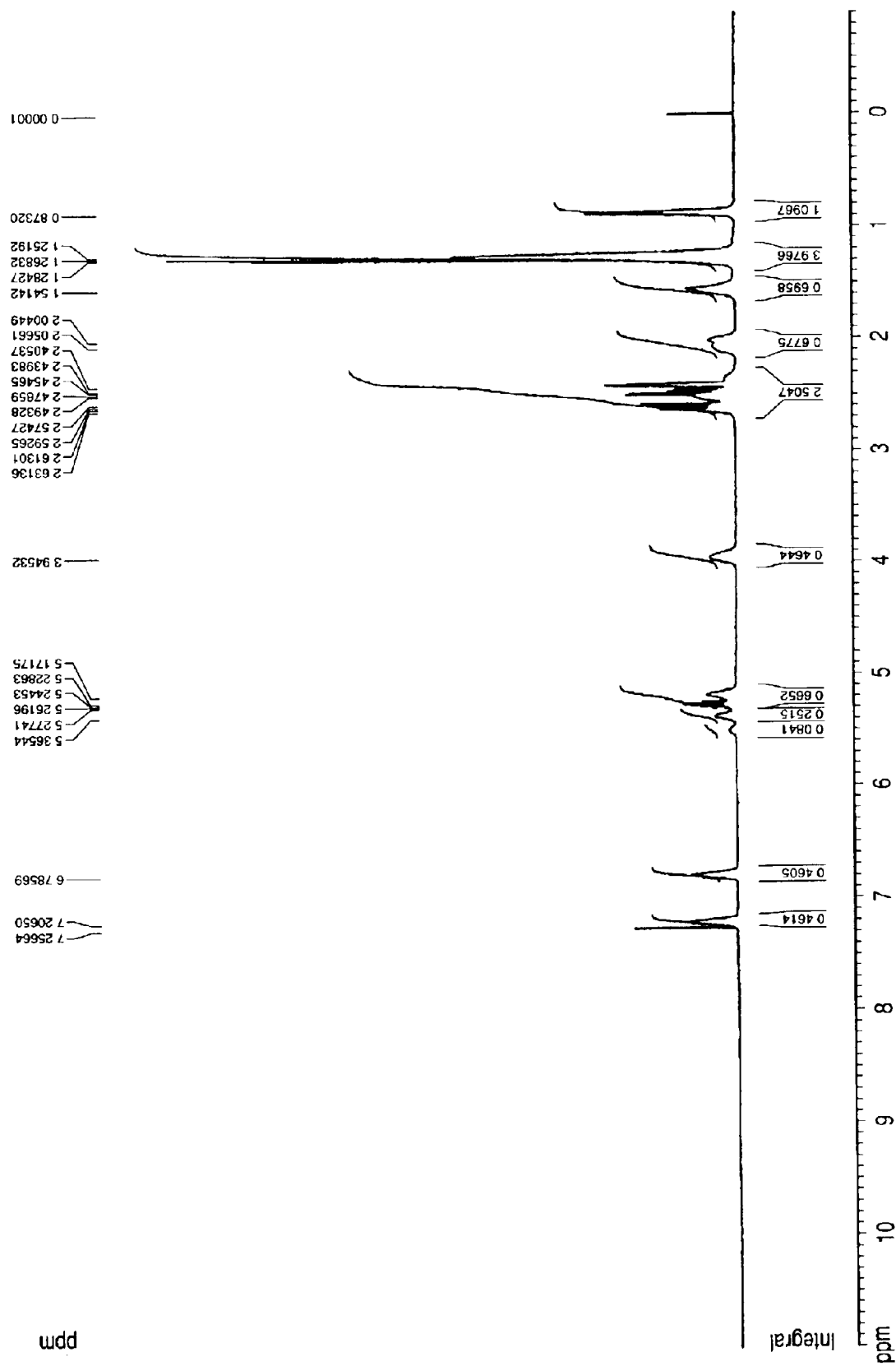
FIGURE

POLYHYDROXYALKANOATE THAT COMPRISES UNIT HAVING (METHYLSULFANYL) PHENOXY STRUCTURE IN SIDE CHAIN THEREOF AND PROCESS FOR PRODUCING THE SAME

BACKGROUND OF THE INVENTION

1. Field of the Invention

The present invention relates to a polyhydroxyalkanoate (PHA) that comprises a novel structural unit and a process for producing the same. More particularly, the present invention relates to a novel biodegradable PHA that comprises 3-hydroxyalkanoic acid units having a (methylsulfanyl)phenoxy group at the end of the side chain thereof, and to a process for producing PHAs from an alkanoic acid having a (methylsulfanyl)phenoxy group at the end of the side chain thereof by using a microorganism capable of producing PHA and accumulating it in the cell.

2. Related Background Art

It has been reported that various microorganisms can produce poly-3-hydroxybutyrate (hereinafter, also referred to as "PHB" for short) or other PHA and accumulate it in the cell ("Biodegradable Plastics Handbook", Biodegradable Plastics Society Ed., NTS, pages 178–197 (1995)). These polymers may be utilized for production of various products by, for example, melt processing as with conventional plastics, but unlike many conventional synthetic polymer compounds, these polymers do not cause pollution in the natural environment because they are biodegradable, i.e., they are completely degraded by microorganisms in the natural world. Furthermore, they have good biocompatibility and their applications in the medical field as soft materials are expected.

Microbial PHAs are known to have different compositions and/or structures depending on, for example, the type of the microorganism, compositions of the culture medium, and culture conditions. Thus, studies have been done to control the composition and structure to improve physical properties of PHA. For instance, *Alcaligenes eutrophus* H16 (ATCC No. 17699) and mutants thereof are known to produce copolymers of 3-hydroxybutyrate and 3-hydroxyvalerate (hereinafter, abbreviated as 3HV) with various composition ratios (Japanese Patent Publication No. 6-15604 and Japanese Patent Publication No. 7-14352 and Japanese Patent Publication No. 8-19227).

Japanese Patent No. 2642937 discloses production of PHA of $C_6$ to $C_{12}$ 3-hydroxyalkanoate monomer units by feeding acyclic aliphatic hydrocarbon compounds as substrates to *Pseudomonas oleovorans* (ATCC No. 29347).

Japanese Patent Application Laid-Open No. 5-7492 discloses a process for producing a copolymer of 3HB and 3HV using a microorganism such as *Methylobacterium* sp., *Paracoccus* sp., *Alcaligenes* sp., and *Pseudomonas* sp. in contact with $C_3$ to $C_7$ primary alcohol.

Japanese Patent Application Laid-Open No. 5-93049 and Japanese Patent Application Laid-Open No. 7-265065 disclose production of two-component copolymers of 3HB and 3-hydroxyhexanate by cultivating *Aeromonas caviae* with oleic acid or olive oil as a substrate.

Japanese Patent Application Laid-Open No. 9-191893 discloses that *Comamonas acidovorans* IFO 13852 produces polyester containing 3HB and 4-hydroxybutyrate as the monomer units when it is cultivated in the presence of gluconic acid and 1,4-butanediol as substrates.

Further, certain microorganisms have already been known to produce PHAs having various substituents introduced such as unsaturated hydrocarbons, ester groups, cyano groups, halogenated hydrocarbons, and epoxides. For example, Macromol. Chem., 191, 1957–1965 (1990), Macromolecules, 24, 5256–5260 (1991), and Chirality, 3, 492–494 (1991) report that *Pseudomonas oleovorans* produces PHAs containing 3-hydroxy-5-phenylvalerate (hereinafter, abbreviated as 3HPV) as the monomer unit, where changes in physical properties of the PHA are observed probably due to the presence of 3HPV.

Of the PHAs having a substituent on the side chain thereof, lately those having a phenoxy group on the side chain have been actively developed.

It has been reported that *Pseudomonas oleovorans* produces from 11-phenoxyundecanoic acids PHA made with monomer units of 3-hydroxy-5-phenoxyvalerate and 3-hydroxy-9-phenoxynonanoate (Macromol. Chem. Phys., 195, 1665–1672 (1994)).

Macromolecules, 29, 3432–3435 (1996) reports production of PHA having monomer units of 3-hydroxy-4-phenoxybutyrate and 3-hydroxy-6-phenoxyhexanoate from 6-phenoxyhexanoic acids; production of PHA having units of 3-hydroxy-4-phenoxybutyrate, 3-hydroxy-6-phenoxyhexanoate, 3-hydroxy-4-phenoxybutyrate, 3-hydroxy-6-phenoxyhexanoate and 3-hydroxy-8-phenoxyoctanoate from 8-phenoxyoctanoic acid; and production of PHA made with units of 3-hydroxy-5-phenoxyvaleric acid and 3-hydroxy-7-phenoxyheptanoic acid from 11-hydroxyundecanoic acid, by using *Pseudomonas oleovorans*.

Can. J. Microbiol., 41, 32–43 (1995) reports production of PHAs containing 3-hydroxy-6-(4-cyanophenoxy)hexanoic acids or 3-hydroxy-6-(4-nitrophenoxy)hexanoic acid as the monomer units by *Pseudomonas oleovorans* ATCC 29347 or *Pseudomonas putida* KT 2422 using octanoic acid and 6-(4-cyanophenoxy)hexanoic acid or 6-(p-nitrophenoxy)hexanoic acid as a substrate.

Recently, PHAs having phenoxy group on the side chain thereof have been actively developed, especially those having functional groups such as fluoro, cyano, and nitro introduced onto the phenoxy aromatic ring of the side chain. Although there are many reports about such PHA, the species are limited to those described above, and no report on PHAs having novel functional groups.

SUMMARY OF THE INVENTION

Accordingly, an object of the present invention is to provide a novel PHA that contains a novel monomer unit having a functional (methylsulfanyl) group on the aromatic ring of the phenoxy group on the side chain thereof and a process for producing the same.

In one aspect, the present invention provides a polyhydroxyalkanoate comprising a unit represented by the following chemical formula (1):

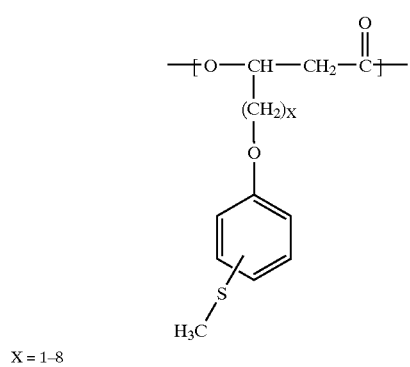

X = 1–8 wherein x represents an integer of 1 to 8 being the same or different each other in the polyhydroxyalkanoate.

In one embodiment, the polyhydroxyalkanoate further comprises one or more units selected from 3-hydroxyalkanoates and 3-hydroxyalkenoates.

Specifically, the present invention provides a polyhydroxyalkanoate that comprises a 3-hydroxy-5-[4-(methylsulfanyl)phenoxy]valerate unit represented by the chemical formula (4):

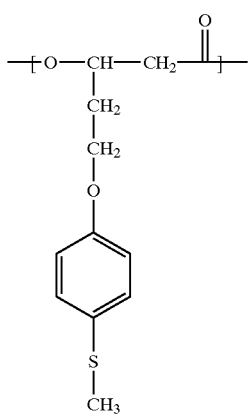

(4)

In another aspect, the present invention provides a process which process comprises the step of culturing a PHA-producing microorganism in a culture medium containing corresponding ω-[(methylsulfanyl)phenoxy]alkanoic acid represented by the following chemical formula (5):

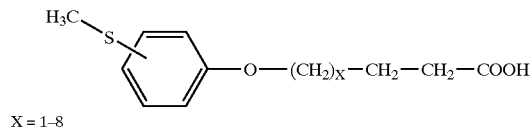

(5)

X = 1–8 wherein X is an integer of 1 to 8, for producing the above-described polyhydroxyalkanoate.

In one embodiment, the ω-[(methylsulfanyl)phenoxy] alkanoic acid is 5-[4-(methylsulfanyl)phenoxy]valeric acid represented by the following chemical formula (6):

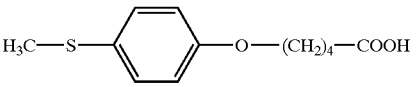

(6)

The PHA of the present invention is useful as a functional polymer, with potential utility as device materials and medicament materials.

The PHA production process of the present invention enables efficient microbial production of a novel biodegradable PHA containing a 3-hydroxy-ω-[(methylsulfanyl)phenoxy]alkanoate unit from corresponding ω-[(methylsulfanyl)phenoxy]alkanoic acid.

BRIEF DESCRIPTION OF THE DRAWING

FIGURE shows the $^1$H-NMR spectrum of a polyhydroxyalkanoate obtained in Example 1.

DETAILED DESCRIPTION OF THE PREFERRED EMBODIMENTS

A novel polyhydroxyalkanoate according to the present invention has a (methylsulfanyl)phenoxy structure on the side chain of a hydroxyalkanoate unit. This structure provides physical and chemical properties that are significantly different from those of known microbial polyhydroxyalkanoates.

The polyhydroxyalkanoate of the present invention contains a unit represented by the following chemical formula (1):

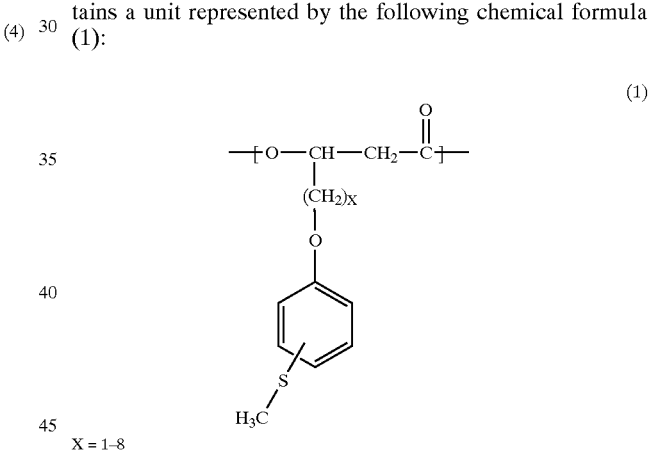

(1)

X = 1–8 wherein x represents an integer of 1 to 8 being the same or different each other in the polyhydroxyalkanoate.

In addition to the above-described monomer unit, the polyhydroxyalkanoate of the present invention may contain one or more units selected from 3-hydroxyalkanoates and 3-hydroxyalkenoates represented by the following chemical formulae (2) and (3) respectively:

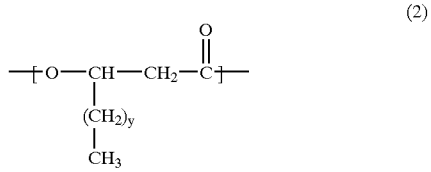

(2)

y = 0–8 wherein y represents an integer of 0 to 8 being the same or different each other in the polyhydroxyalkanoate;

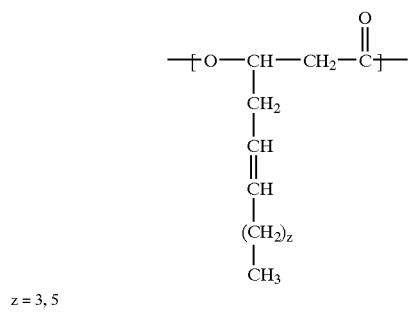

$z = 3, 5$ wherein z is an integer of 3 or 5 being the same or different in the polyhydroxyalkanoate.

The polyhydroxyalkanoate of the present invention has typically a number average molecular weight of 5,000 to 300,000.

The novel polyhydroxyalkanoate according to the present invention can be produced by the steps of: culturing a PHA producing microorganism in a culture medium containing a growth substrate and a ω-[(methylsulfanyl)phenoxy] alkanoic acid as a feedstock; and recovering polyhydroxyalkanoate containing units having a (methylsulfanyl) phenoxy group at the end of the side chain thereof produced by and accumulated in the microorganism during the cultivation step. In the microbial PHAs, the carbons at the 3 position of all 3-hydroxyalkanoate units including those represented by the chemical formula (1) are asymmetric carbons whose absolute configuration is R, indicating the biodegradability thereof.

The present invention is described more in detail below.

PHA-Producing Microorganisms

In the process for producing PHAs according to the present invention, any microorganisms can be used to produce PHA containing a unit having a (methylsulfanyl) phenoxy group at the end of the side chain thereof so long as the microorganism can produce and accumulate the subject PHA in the cells when cultivated in a culture medium containing a corresponding ω-[(methylsulfanyl)phenoxy] alkanoic acid represented by the chemical formula (5) as the source compound. For example, the microorganisms may be those belonging to the genus Pseudomonas having PHA-producing capabilities.

Examples of suitable microorganisms of genus *Pseudomonas* include the following three strains: *Pseudomonas cichorii* YN2 (FERM BP-7375), *Pseudomonas cichorii* H45 (FERM BP-7374), and *Pseudomonas jessenii* P161 (FERM BP-7376). These three microorganisms was first deposited as the national deposit by the applicant, and is deposited as the international deposit under the Budapest Treaty under the above-mentioned accession numbers in International Patent Organism Depositary, National Institute of Advanced Industrial Science and Technology, Independent Administrative Institution, Ministry of Economy, Trade and Industry, 1–3, Higashi 1-chome, Tsukuba-shi, Ibaraki-ken 305-8566, JAPAN (former National Institute of Bioscience and Human-Technology (NIBH) of the Agency of Industrial Science and Technology, Ministry of Economy, Trade and Industry). They are also described in Japanese Patent Application Laid-Open No. 2002-80571) as novel strains capable of producing PHAs.

Bacteriological properties of the strains YN2, H45, and P161 are given below.

Bacteriological Properties of Strain YN2
(1) Morphological Properties
Shape and size of cells: rod, 0.8 μm×1.5 to 2.0 μm
Polymorphism of cells: negative
Mobility: motile
Sporulation: negative
Gram staining: negative
Colony shape: circular; entire, smooth margin; low convex; smooth surface; glossy; translucent
(2) Physiological Properties
Catalase: positive
Oxidase: positive
O/F test: oxidative (non-fermentative)
Nitrate reduction: negative
Indole production: positive
Acid production from glucose: negative
Arginine dihydrolase: negative
Urease: negative
Esculin hydrolysis: negative
Gelatin hydrolysis: negative
β-Galactosidase: negative
Fluorescent pigment production on King's B agar: positive
Growth under 4% NaCl: positive (weak growth)
Poly-β-hydroxybutyrate accumulation: negative (*)
Tween 80 hydrolysis: positive
(*) Colonies cultured on nutrient agar were stained with Sudan Black for determination.
(3) Substrate Assimilation
Glucose: positive
L-Arabinose: positive
D-Mannose: negative
D-Mannitol: negative
N-Acetyl-D-glucosamine: negative
Maltose: negative
Potassium gluconate: positive
n-Caprate: positive
Adipate: negative
dl-Malate: positive
Sodium citrate: positive
Phenyl acetate: positive Bacteriological Properties of Strain H45
(1) Morphological Properties
Shape and size of cells: rod, 0.8 μm×1.0 to 1.2 μm
Polymorphism of cells: negative
Mobility: motile
Sporulation: negative
Gram staining: negative
Colony shape: circular; entire, smooth margin; low convex; smooth surface; glossy; cream-colored
(2) Physiological Properties
Catalase: positive
Oxidase: positive
O/F test: oxidative
Nitrate reduction: negative
Indole production: negative
Acid production from glucose: negative
Arginine dihydrolase: negative
Urease: negative
Esculin hydrolysis: negative
Gelatin hydrolysis: negative
β-Galactosidase: negative
Fluorescent pigment production on King's B agar: positive
Growth under 4% NaCl: negative
Poly-β-hydroxybutyrate accumulation: negative
(3) Substrate Assimilation
Glucose: positive
L-Arabinose: negative D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive Bacteriological Properties of Strain P161
(1) Morphological Properties
Shape and size of cells: sphere, ϕ0.6 µm, rods, 0.6 µm×1.5 to 2.0 µm
Polymorphism of cells: elongated form
Mobility: motile
Sporulation: negative
Gram staining: negative
Colony shape: circle; entire, smooth margin; low convex; smooth surface; pale yellow
(2) Physiological Properties
Catalase: positive
Oxidase: positive
O/F test: oxidative
Nitrate reduction: positive
Indole production: negative
Acid production from glucose: negative
Arginine dihydrolase: positive
Urease: negative
Esculin hydrolysis: negative
Gelatin hydrolysis: negative
β-Galactosidase: negative
Fluorescent pigment production on King's B agar: positive
(3) Substrate Assimilation
Glucose: positive
L-Arabinose: positive
D-Mannose: positive
D-Mannitol: positive
N-Acetyl-D-glucosamine: positive
Maltose: negative
Potassium gluconate: positive
n-Caprate: positive
Adipate: negative
dl-Malate: positive
Sodium citrate: positive
Phenyl acetate: positive In addition to the above-described strains of *Pseudomonas* sp., it is possible to use strains belonging to genus *Aeromonas*, genus *Commamonas*, and genus *Burkholderia*, capable of producing PHA containing a 3-hydroxy-ω-[(methylsulfanyl)phenoxy]alkanoate unit utilizing an ω-[(methylsulfanyl)phenoxy]alkanoic acid as a feedstock.

Cultivation

According to the PHA production process of the present invention, by culturing the above-mentioned microorganism capable of producing PHA in a culture medium containing ω-[(methylsulfanyl)phenoxy]alkanoic acid represented by the above chemical formula (5) as a feedstock, PHA represented by the chemical formula (1) containing 3-hydroxyalkanate units having a (methylsulfanyl)phenoxy group at the end of the side chain thereof is produced and accumulated in the cells.

For ordinary culture of the microorganisms used in the present invention, for example, for preparation of stock strains, or for obtaining cells or maintaining activities required in PHA production, culture media are selected to contain ingredients necessary for the proliferation of the microorganisms used. For example, any one of known culture media, such as typical natural culture media (e.g., nutrient broth, yeast extract) and synthetic culture media supplemented with nutrients, may be used as long as the culture medium does not adversely affect the growth and survival of the microorganisms. Cultivation conditions such as temperature, aeration and agitation are appropriately selected depending on the microorganisms used.

In order to produce the subject PHA by using the PHA-producing microorganism as described above, an inorganic culture medium may be used that contains at least a growth substrate for the microorganism and a compound represented by the above chemical formula (5) corresponding to the monomer unit as the feedstock for PHA production. It is desirable that the compound represented by the above chemical formula (5) be contained in an amount of 0.01% to 1% (w/v), and more preferably 0.02% to 0.2% (w/v), per a culture medium. The compound represented by the chemical formula (5) does not always have good water solubility. However, with the microorganisms indicated herein, suspension would cause no trouble.

The feedstock compound to be added to the culture medium may be one or more compounds represented by the chemical formula (5), such as 5-[4-(methylsulfanyl)phenoxy]valerate and 6-[4-(methylsulfanyl)phenoxy]hexanoic acid, for example.

The feedstock compound represented by the chemical formula (5) may be, in some cases, added to the culture medium as a solution or suspension in a solvent such as 1-hexadecene or n-hexadecane in order to improve dispersibility. In such a case, the concentration of the solvent is required to be equal to or lower than 3% (v/v) relative to the solution of the culture medium.

It is preferable to add a growth substrate for microbial proliferation to the culture medium separately. As the growth substrate, nutrients such as yeast extract, polypeptone, and meat extract may be used. The growth substrate may be selected based on the usefulness as the substrate to the strain to be used, from saccharides, organic acids generated in the TCA cycle, organic acids or salts thereof generated from the biochemical reactions one or two steps later than the TCA cycle, amino acids or salts thereof, $C_4$ to $C_{12}$ straight chain alkanoic acids or salts thereof.

One or more saccharides may suitably be used selected from aldose such as glyceraldehyde, erythrose, arabinose, xylose, glucose, galactose, mannose, and fructose; alditol such as glycerol, erythritol, and xylitol; aldonic acids such as gluconic acid; uronic acid such as glucuronic acid and galacturonic acid; and disaccharide such as maltose, sucrose, and lactose.

As the organic acids or salts thereof, one or more compounds may suitably be selected from pyruvic acid, malic acid, lactic acid, citric acid, succinic acid, and salts thereof.

As the amino acids or salts thereof, one or more compounds may suitably be selected from glutamic acid, aspartic acid, and salts thereof.

Of these, polypeptone and saccharides are preferable. Preferable saccharides include at least one selected from glucose, fructose, and mannose. Preferably, the substrate is contained in an amount of 0.1% to 5% (w/v), and more preferably 0.2% to 2% (w/v) in the culture medium.

Sometimes the microbial PHA productivity is improved when the microorganism is fully grown and then transferred to a culture medium in which nitrogen source such as ammonium chloride is limited and a compound serving as a substrate for PHA is added. For example, a multi-step approach may be used that performs two or more steps successively under different cultivation conditions.

More specifically, a microorganism is grown in a culture medium that contains a compound represented by the chemical formula (5) and polypeptone until from late logarithmic phase to stationary phase (step 1-1), and then collected by using, for example, centrifugation. Subsequently, the microorganism cultivated in the step 1-1 is further cultivated in a culture medium that contains a compound represented by the chemical formula (5) and an organic acid or a salt thereof as described above (preferably without a nitrogen source) (step 1-2). Alternatively, the microorganism is cultured in a culture medium that contains a compound represented by the chemical formula (5) and a saccharide as described above until from late logarithmic phase to stationary phase (step 1-3), and collected by using, for example, centrifugation. Subsequently, the microorganism grown in the step 1-3 is further cultivated in a culture medium that contains the compound represented by the chemical formula (5) and a saccharide as described above (preferably without a nitrogen source) (step 1-4).

The cultivation temperature should be a temperature at which the above-mentioned strains can proliferate well. For example, the cultivation temperature may be 15° C. to 40° C., preferably 20° C. to 35° C., and more preferably 20° C. to 30° C.

The cultivation may be performed by any suitable cultivation techniques such as liquid or solid cultivation, with which the above-mentioned microorganisms can proliferate to produce polyhydroxyalkanoates. Furthermore, the type of the cultivation is not limited as long as oxygen is supplied properly. Examples include batch cultivation, fed batch cultivation, semi-continuous cultivation, and continuous cultivation. In liquid batch cultivation, the oxygen may be supplied while shaking the content of a shake flask. Alternatively, the oxygen may be supplied by means of an agitation-ventilation method using a jar fermenter.

As the inorganic culture medium to be used for the above-mentioned cultivation procedure, any culture medium may be used that contains ingredients that are required for the proliferation of the microorganisms, such as a phosphorous source (e.g., phosphates) and a nitrogen source (e.g., ammonium salts, nitrates). For example, MSB medium and M9 medium may be used.

The composition of an inorganic culture medium (M9 medium) that is used in a process according to the present invention is given below.

(M9 Medium)

| | |
|---|---|
| Na$_2$HPO$_4$ | 6.2 g |
| KH$_2$PO$_4$ | 3.0 g |
| NaCl | 0.5 g |
| NH$_4$Cl | 1.0 g |

(in 1 liter culture medium; pH 7.0)

In order to ensure good proliferation, and production of the polyhydroxyalkanoates, it is necessary to add a trace ingredient solution that is indicated below in an amount of about 0.3% (v/v) to the above-mentioned inorganic culture medium.

(Trace Ingredient Solution)

| | |
|---|---|
| Nitrilotriacetic Acid | 1.5 g |
| MgSO$_4$ | 3.0 g |
| MnSO$_4$ | 0.5 g |
| NaCl | 1.0 g |
| FeSO$_4$ | 0.1 g |
| CaCl$_2$ | 0.1 g |
| CoCl$_2$ | 0.1 g |
| ZnSO$_4$ | 0.1 g |
| CuSO$_4$ | 0.1 g |
| AlK(SO$_4$)$_2$ | 0.1 g |
| H$_3$BO$_3$ | 0.1 g |
| Na$_2$MoO$_4$ | 0.1 g |
| NiCl$_2$ | 0.1 g |

(in 1 liter solution; pH 7.0)

PHA Recovery

The microorganism used in the present invention produces and accumulates the subject PHA in the cell. Therefore, in the PHA production process of the present invention, a step of recovering the subject PHA from the cells is provided after the cultivation.

For the purpose of recovering the PHA from the cells, a solvent extraction technique is used, in which a solubilized polyhydroxyalkanoate is separated from insoluble cell components. A standard chloroform extraction technique is the most convenient and simple but a solvent other than chloroform may be used such as dichloromethane, dioxane, tetrahydrofuran, acetonitrile, and acetone. In environments where it is difficult to use an organic solvent, components of the strains other than the polyhydroxyalkanoates are removed by treating with, for example, a surfactant such as SDS, with an enzyme such as lysozyme, or with EDTA and cellular components are removed to recover only the polyhydroxyalkanoates. Alternatively, one can use cell disruption treatment such as ultrasonic disruption, homogenization, pressure disruption, disruption with glass beads, trituration, grinding and freeze-thawing to separate and recover the polyhydroxyalkanoates accumulated in the cells.

It should be understood that the cultivation of the microorganisms of the present invention, the production of the polyhydroxyalkanoates by the microorganisms of the present invention and accumulation of the polyhydroxyalkanoates in the cell, and the recovery of the polyhydroxyalkanoates from the cell are not limited to the above-mentioned techniques and procedures.

The polyhydroxyalkanoates that are produced by the microorganisms according to the process of the present invention may comprise, in addition to the units represented by the chemical formula (1), 3-hydroxyalkanoic acid units represented by the chemical formula (2) or 3-hydroxyalk-5-enoic acid units represented by the chemical formula (3) that is biosynthesized through a fatty acid synthesizing system by using a proliferation substrate to be added to the culture medium. The carbons at the 3 position of all 3-hydroxyalkanoic acid units contained are asymmetric carbons whose absolute configuration is R, indicating the biodegradability thereof.

PHA of the present invention has utility in various application fields other than use as ordinary plastics, including device materials, medicament materials and medical materials such as medical sheet.

Further, the presence of the (methylsulfanyl)phenoxy group in the units represented by the chemical formula (1)

and the presence of the various substituents positioned on the benzene ring thereof provide new physical and chemical properties to the polymers. Improvements in physical properties of such polymers are expected. The polymers can be expanded to the fields to which they were not applicable in the past.

EXAMPLES

The present invention is described specifically below with reference to examples thereof, but not limited thereto. In the following examples, percentages are by weight unless otherwise specified.

Example 1

*Pseudomonas cichorii* YN2 was inoculated to 200 mL of M9 medium containing 0.5% of polypeptone (Wako Pure Chemical Industries, Ltd.) and 0.1% of 5-[4-(methylsulfanyl)phenoxy]valeric acid and cultured with shaking at 125 strokes/min at 30° C. for 48 hours. Then, the cells were collected by centrifugation, re-suspended in 200 mL of M9 medium containing 0.5% of sodium pyruvate and 0.1% of 5-[4-(methylsulfanyl)phenoxy]valeric acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 28 mg of polyhydroxyalkanoate.

The molecular weight of the polyhydroxyalkanoate was determined by gel permeation chromatography (GPC; TOSOH HLC-8220, column; TOSOH TSK-GEL SuperHM-H (trade name), solvent; chloroform, polystyrene equivalent). As a result, Mn was 15,600 and Mw was 36,000.

The polyhydroxyalkanoate was further subjected to NMR analysis under the following conditions.

Spectrometer

FT-NMR: Bruker DPX 400 with spectrometer frequencies of 400 MHz for $^1$H-NMR.

Conditions

Nuclear Species: $^1$H
Solvent: $CDCl_3$
Temperature: room temperature

FIGURE shows $^1$H-NMR spectra of the polyhydroxyalkanoate. Identification results thereof are given in Table 1.

TABLE 1

| Chemical shifts (ppm) | Integration | Splitting patterns | Identification |
| --- | --- | --- | --- |
| 2.02 | 2H | br | d1 |
| 2.40 | 3H | s | l1 |
| 2.43–2.63 | 2H | m | b1 |
| 3.94 | 2H | br | e1 |
| 5.27 | 1H | br | c1 |
| 6.79 | 2H | br | g1, k1 |
| 7.25 | 2H | br | h1, j1 |

As clearly shown by Table 1, it was confirmed that the polyhydroxyalkanoate is one represented by the following chemical formula (7) containing, as the monomer units, 3-hydroxy-5-[4-(methylsulfanyl)phenoxy]valerate, and 3-hydroxyalkanoates having 4 to 12 carbon atoms such as 3-hydroxybutyric acid and 3-hydroxyvaleric acid, and 3-hydroxyalkenoate.

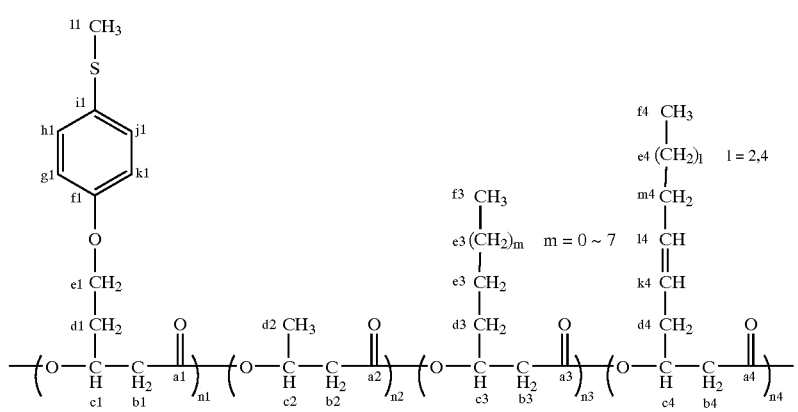

(7)

The integration of the $^1$H-NMR spectra indicated that the polyhydroxyalkanoate contains 3-hydroxy-5-[4-(methylsulfanyl)phenoxy]valerate by 23.0 mol %.

Example 2

*Pseudomonas cichorii* H45 was inoculated to 200 mL of M9 medium containing 0.5% of polypeptone (Wako Pure Chemical Industries, Ltd.) and 0.1% of 5-[4-(methylsulfanyl)phenoxy]valeric acid and cultured with shaking at 125 strokes/min at 30° C. for 48 hours. Then, the cells were collected by centrifugation, re-suspended in 200 mL of M9 medium containing 0.5% of sodium pyruvate and 0.1% of 5-[4-(methylsulfanyl)phenoxy]valeric acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 11 mg of polyhydroxyalkanoate.

The polyhydroxyalkanoate obtained was subjected to molecular weight determination and NMR analysis under the same conditions as in Example 1. As a result, it was revealed that this polyhydroxyalkanoate is one represented by the chemical formula (7) containing, as the monomer units, 3-hydroxy-5-[4-(methylsulfanyl)phenoxy]valerate, and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 3-hydroxy-5-[4-(methylsulfanyl)phenoxy]valerate by 21.4 mol %.

Example 3

*Pseudomonas jessenii* P161 was inoculated to 200 mL of M9 medium containing 0.5% of polypeptone (Wako Pure Chemical Industries, Ltd.) and 0.1% of 5-[4-(methylsulfanyl)phenoxy]valeric acid and cultured with shaking at 125 strokes/min at 30° C. for 48 hours. Then, the cells were collected by centrifugation, re-suspended in 200 mL of M9 medium containing 0.5% of sodium pyruvate and 0.1% of 5-[4-(methylsulfanyl)phenoxy]valeric acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 9 mg of polyhydroxyalkanoate.

The polyhydroxyalkanoate obtained was subjected to molecular weight determination and NMR analysis under the same conditions as in Example 1. As a result, it was revealed that this polyhydroxyalkanoate is one represented by the chemical formula (7) containing, as the monomer units, 3-hydroxy-5-[4-(methylsulfanyl)phenoxy]valerate, and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 3-hydroxy-5-[4-(methylsulfanyl)phenoxy]valerate by 18.4 mol %.

Example 4

*Pseudomonas cichorii* YN2 was inoculated to 200 mL of M9 medium containing 0.5% of D-glucose and 0.1% of 5-[4-(methylsulfanyl)phenoxy]valeric acid and cultured with shaking at 125 strokes/min at 30° C. for 48 hours. Then, the cells were collected by centrifugation, re-suspended in 200 mL of M9 medium containing 0.5% of D-glucose and 0.1% of 5-[4-(methylsulfanyl)phenoxy]valeric acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 18 mg of polyhydroxyalkanoate.

The polyhydroxyalkanoate obtained was subjected to molecular weight determination and NMR analysis under the same conditions as in Example 1. As a result, it was revealed that this polyhydroxyalkanoate is one represented by the chemical formula (7) containing, as the monomer units, 3-hydroxy-5-[4-(methylsulfanyl)phenoxy]valerate, and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 3-hydroxy-5-[4-(methylsulfanyl)phenoxy]valerate by 29.6 mol %.

Example 5

*Pseudomonas cichorii* H45 was inoculated to 200 mL of M9 medium containing 0.5% of D-glucose and 0.1% of 5-[4-(methylsulfanyl)phenoxy]valeric acid and cultured with shaking at 125 strokes/min at 30° C. for 48 hours. Then, the cells were collected by centrifugation, re-suspended in 200 mL of M9 medium containing 0.5% of D-glucose and 0.1% of 5-[4-(methylsulfanyl)phenoxy]valeric acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 µm and concentrated by a rotary evaporator. The concentrated solution was precipitated with cold methanol. The precipitate was recovered and dried in vacuum to yield 18 mg of polyhydroxyalkanoate.

The polyhydroxyalkanoate obtained was subjected to molecular weight determination and NMR analysis under the same conditions as in Example 1. As a result of NMR, it was revealed that this polyhydroxyalkanoate is one represented by the chemical formula (7) containing, as the monomer units, 3-hydroxy-5-[4-(methylsulfanyl)phenoxy]valerate, and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 3-hydroxy-5-[4-(methylsulfanyl)phenoxy]valerate by 35.6 mol %.

Example 6

*Pseudomonas cichorii* YN2 was inoculated to 200 mL of M9 medium containing 0.5% of yeast extract (DIFCO) and 0.1% of 5-[4-(methylsulfanyl)phenoxy]valeric acid and cultured with shaking at 125 strokes/min at 30° C. for 48 hours. Then, the cells were collected by centrifugation, re-suspended in 200 mL of M9 medium containing 0.5% of sodium pyruvate and 0.1% of 5-[4-(methylsulfanyl) phenoxy]valeric acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 15 mg of polyhydroxyalkanoate.

The polyhydroxyalkanoate obtained was subjected to molecular weight determination and NMR analysis under the same conditions as in Example 1. As a result of NMR, it was revealed that this polyhydroxyalkanoate is one represented by the chemical formula (7) containing, as the monomer units, 3-hydroxy-5-[4-(methylsulfanyl)phenoxy] valerate, and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 3-hydroxy-5-[4-(methylsulfanyl)phenoxy]valerate by 15.1 mol %.

Example 7

Pseudomonas cichorii YN2 was inoculated to 200 mL of M9 medium containing 0.5% of sodium glutamate and 0.1% of 5-[4-(methylsulfanyl)phenoxy]valeric acid and cultured with shaking at 125 strokes/min at 30° C. for 48 hours. Then, the cells were collected by centrifugation, re-suspended in 200 mL of M9 medium containing 0.5% of sodium pyruvate and 0.1% of 5-[4-(methylsulfanyl)phenoxy]valeric acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 25 mg of polyhydroxyalkanoate.

The polyhydroxyalkanoate obtained was subjected to molecular weight determination and NMR analysis under the same conditions as in Example 1. As a result of NMR, it was revealed that this polyhydroxyalkanoate is one represented by the chemical formula (7) containing, as the monomer units, 3-hydroxy-5-[4-(methylsulfanyl)phenoxy] valerate, and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 3-hydroxy-5-[4-(methylsulfanyl)phenoxy]valerate by 12.2 mol %.

Example 8

Pseudomonas cichorii YN2 was inoculated to 200 mL of M9 medium containing 0.5% of polypeptone (Wako Pure Chemical Industries, Ltd.) and 0.1% of 5-[4-(methylsulfanyl)phenoxy]valeric acid and cultured with shaking at 125 strokes/min at 30° C. for 48 hours. Then, the cells were collected by centrifugation, re-suspended in 200 mL of M9 medium containing 0.1% of nonanoic acid and 0.1% of 5-[4-(methylsulfanyl)phenoxy]valeric acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 30 mg of polyhydroxyalkanoate.

The polyhydroxyalkanoate obtained was subjected to molecular weight determination and NMR analysis under the same conditions as in Example 1. As a result NMR, it was revealed that this polyhydroxyalkanoate is one represented by the chemical formula (7) containing, as the monomer units, 3-hydroxy-5-[4-(methylsulfanyl)phenoxy] valerate, and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 3-hydroxy-5-[4-(methylsulfanyl)phenoxy]valerate by 3.1 mol %.

Table 2 shows the dry weight of the cells, the dry weight of the polymer, the ratio of the polymer to the cells by dry weight, and the amount (mol %) of the 3-hydroxy-5-[(phenylmethyl)sulfanyl]valerate (abbreviated as "3HMSPxV") unit in the resulting polymer in Examples 1 to 8.

TABLE 2

|  | Cell Dry Weight (mg/L) | Polymer Dry Weight (mg/L) | Polymer Weight/ Cell Weight (%) | 3HMSPxV Unit mol % |
| --- | --- | --- | --- | --- |
| Example 1 | 800 | 140 | 17.5 | 23.0 |
| Example 2 | 505 | 55 | 10.9 | 21.4 |
| Example 3 | 455 | 45 | 9.9 | 18.4 |
| Example 4 | 630 | 135 | 21.4 | 29.6 |
| Example 5 | 520 | 90 | 17.3 | 35.6 |
| Example 6 | 615 | 75 | 12.2 | 17.5 |
| Example 7 | 585 | 125 | 21.4 | 12.2 |
| Example 8 | 500 | 150 | 30.0 | 3.1 |

Table 3 shows the molecular weight of the resulting polymer in Examples 1 to 8.

TABLE 3

|  | Number average molecular weight (Mn) | Weight average molecular weight (Mw) |
| --- | --- | --- |
| Example 1 | 15,600 | 36,000 |
| Example 2 | 16,400 | 37,500 |
| Example 3 | 16,200 | 37,100 |
| Example 4 | 15,100 | 34,700 |
| Example 5 | 15,400 | 35,200 |
| Example 6 | 16,200 | 36,600 |
| Example 7 | 14,800 | 34,500 |
| Example 8 | 18,000 | 39,000 |

Example 9

Pseudomonas cichorii YN2 was inoculated to 200 mL of M9 medium containing 0.5% of polypeptone (Wako Pure Chemical Industries, Ltd.) and 0.1% of 6-[4-(methylsulfanyl)phenoxy]hexanoic acid represented by the chemical formula (8) and cultured with shaking at 125 strokes/min at 30° C. for 48 hours. Then, the cells were collected by centrifugation, re-suspended in 200 mL of M9 medium containing 0.5% of pyruvic acid and 0.1% of 6-[4-(methylsulfanyl)phenoxy]hexanoic acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 22 mg of polyhydroxyalkanoate.

The molecular weight of the polyhydroxyalkanoate was determined by gel permeation chromatography (GPC; TOSOH HLC-8220, column; TOSOH TSK-GEL Super HM-H (trade name), solvent; chloroform, polystyrene equivalent). As a result, Mn was 14,500 and Mw was 33,000.

The polyhydroxyalkanoate obtained was subjected to molecular weight determination and NMR analysis under the same conditions as in Example 1. As a result NMR, it was revealed that this polyhydroxyalkanoate is one containing, as the monomer units, 3-hydroxy-6-[4-(methylsulfanyl)phenoxy]hexanoate represented by the chemical formula (9), 3-hydroxy-4-[4-(methylsulfanyl)phenoxy]butyrate represented by the chemical formula (10) and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 8.1 mol % of 3-hydroxy-6-[4-(methylsulfanyl)phenoxy]hexanoate unit and 9.2 mol % of 3-hydroxy-4-[4-(methylsulfanyl)phenoxy]butyrate unit.

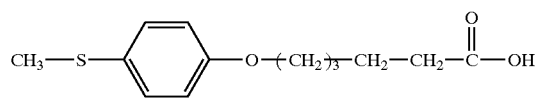

(8)

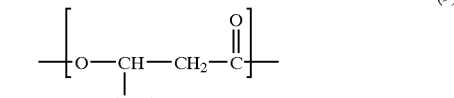

(9)

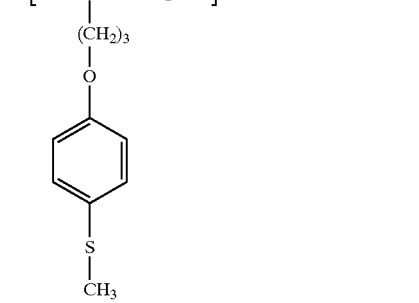

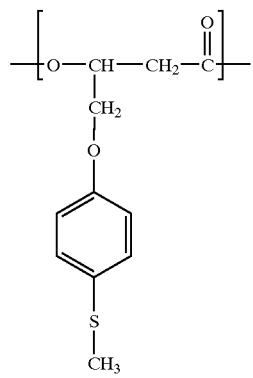

(10)

Example 10

*Pseudomonas cichorii* H45 was inoculated to 200 mL of M9 medium containing 0.5% of D-glucose and 0.1% of 6-[4-(methylsulfanyl)phenoxy]hexanoic acid and cultured with shaking at 125 strokes/min at 30° C. for 48 hours. Then, the cells were collected by centrifugation, re-suspended in 200 mL of M9 medium containing 0.5% of D-glucose and 0.1% of 6-[4-(methylsulfanyl)phenoxy]hexanoic acid but no nitrogen source ($NH_4Cl$), and cultured at 30° C. with shaking at 125 strokes/min for 46 hours. After that, the cells were collected by centrifugation, washed once with cold methanol, and lyophilized. The weight of the lyophilized cells was weighed (the cell dry weight).

The lyophilized pellet was suspended in 20 mL of chloroform and stirred at 60° C. for 20 hours to extract polyhydroxyalkanoate. The extract was filtered through a membrane filter of a pore size of 0.45 μm and concentrated by a rotary evaporator. The concentrated solution was precipitated with cold methanol. The precipitate was recovered and dried in vacuum to yield 16 mg of polyhydroxyalkanoate.

The polyhydroxyalkanoate obtained was subjected to molecular weight determination and NMR analysis under the same conditions as in Example 1. As a result NMR, it was revealed that this polyhydroxyalkanoate is one containing, as the monomer units, 3-hydroxy-6-[4-(methylsulfanyl)phenoxy]hexanoate, 3-hydroxy-4-[4-(methylsulfanyl)phenoxy]butyrate and 3-hydroxyalkanoates having 4 to 12 carbon atoms such as 3-hydroxybutyric acid and 3-hydroxyvaleric acid, and 3-hydroxyalkenoate. The integration of the $^1$H-NMR spectra indicated that the polyhydroxyalkanoate contains 12.4 mol % of 3-hydroxy-6-[4-(methylsulfanyl)phenoxy]hexanoate unit and 15.1 mol % of 3-hydroxy-4-[4-(methylsulfanyl)phenoxy]butyrate.

Table 4 shows the dry weight of the cells, the dry weight of the polymer, the ratio of the polymer to the cells by dry weight, and the amount (mol %) of the 3-hydroxy-6-[4-(methylsulfanyl)phenoxy]hexanoate (3HMSPxHx) unit and 3-hydroxy-4-[4-(methylsulfanyl)phenoxy]butyrate (3HMSPxB) unit in the resulting polymer in Examples 9 and 10.

TABLE 4

| | Cell Dry Weight (mg/L) | Polymer Dry Weight (mg/L) | Polymer Weight/ Cell Weight (%) | 3HMSPxHx Unit mol % | 3HMSPxB Unit mol % |
|---|---|---|---|---|---|
| Example 9 | 605 | 110 | 18.2 | 8.1 | 9.2 |
| Example 10 | 485 | 80 | 16.5 | 12.4 | 15.1 |

Table 5 shows the molecular weight of the resulting polymer in Examples 9 and 10.

TABLE 5

| | Number average molecular weight (Mn) | Weight average molecular weight (Mw) |
|---|---|---|
| Example 9 | 14,500 | 33,000 |
| Example 10 | 15,200 | 34,100 |

The present invention has been described in detail with respect to preferred embodiments, and it will now be that changed and modifications may be made without departing from the invention in its broader aspects, and it is the intention, therefore, in the appended claims to cover all such changes and modifications as fall within the true spirit of the invention.

What is claimed is:

1. A polyhydroxyalkanoate comprising a unit represented by the following chemical formula (1):

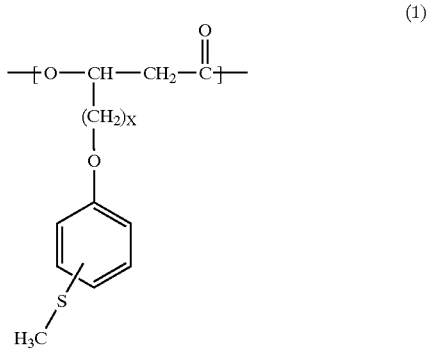

X = 1–8 wherein x is an integer of 1 to 8 being the same or different each other in the polyhydroxyalkanoate.

2. The polyhydroxyalkanoate according to claim 1, further comprising one or more units selected from 3-hydroxyalkanoates and 3-hydroxyalkenoates, the 3-hydroxyalkanoates being represented by the following chemical formula (2):

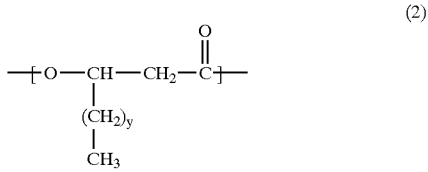

y = 0–8 wherein y represents an integer of 0 to 8 being the same or different each other in the polyhydroxyalkanoate; and 3-hydroxyalkenoates being represented by the following chemical formula (3):

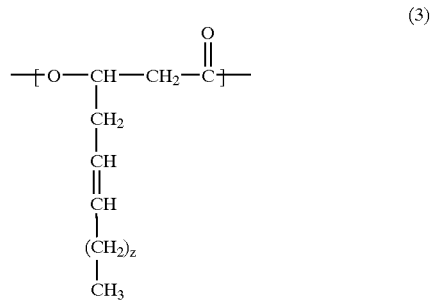

z = 3, 5 wherein z is an integer of 3 or 5 being the same or different in the polyhydroxyalkanoate.

3. The polyhydroxyalkanoate according to claim 1, wherein the polyhydroxyalkanoate has a number average molecular weight of 5,000 to 300,000.

4. The polyhydroxyalkanoate according to claim 1, comprising a 3-hydroxy-5-[4-(methylsulfanyl)phenoxy]valerate unit represented by the following chemical formula (4):

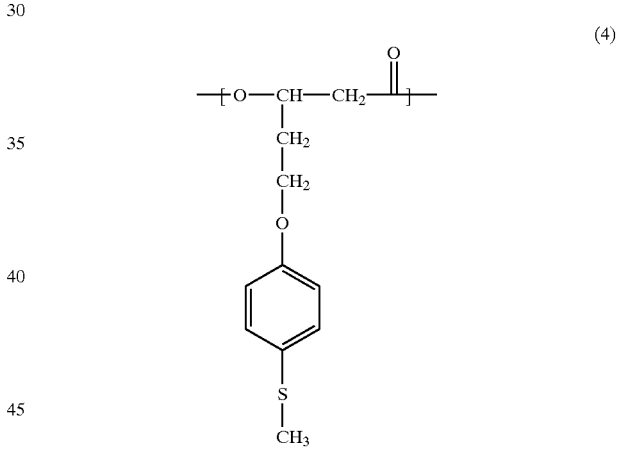

5. A process for producing a polyhydroxyalkanoate comprising the step of culturing a microorganism in a culture medium containing a compound represented by the following chemical formula (5):

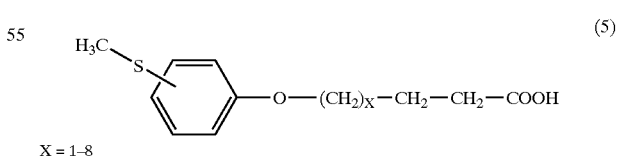

X = 1–8 wherein X is an integer of 1 to 8;

wherein the polyhydroxyalkanoate comprises a unit represented by the following chemical formula (1):

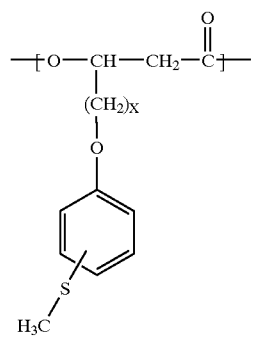

X = 1-8 wherein x is an integer of 1 to 8, being the same or different each other in the polyhydroxyalkanoate.

6. The process according to claim 5, wherein the polyhydroxyalkanoate further comprises one or more units selected from the group consisting of 3-hydroxyalkanoates and 3-hydroxyalkenoates represented by the following chemical formulae (2) and (3):

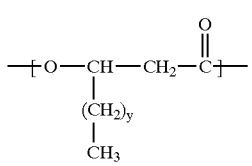

y = 0-8 wherein y is an integer of 0 to 8 being the same or different each other in the polyhydroxyalkanoate,

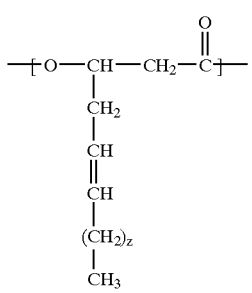

z = 3, 5 wherein z is an integer of 3 or 5, being the same or different in the polyhydroxyalkanoate.

7. The process according to claim 5, wherein the culture medium contains polypeptone.

8. The process according to claim 5, wherein the culture medium contains yeast extract.

9. The process according to claim 5, wherein the culture medium contains a saccharide.

10. The process according to claim 9, wherein the culture medium contains one or more saccharides selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose.

11. The process according to claim 5, wherein the culture medium contains an organic acid or a salt thereof.

12. The process according to claim 11, wherein the culture medium contains one or more organic acids or a salt thereof selected from the group consisting of pyruvic acid, malic acid, lactic acid, citric acid, succinic acid, and salts thereof.

13. The process according to claim 5, wherein the culture medium contains an amino acid or a salt thereof.

14. The process according to claim 13, wherein the culture medium contains one or more amino acid or salts thereof selected from the group consisting of glutamic acid, aspartic acid and salts thereof.

15. The process according to claim 5, wherein the culture medium contains a straight chain alkanoic acid of 4 to 12 carbons or a salt thereof.

16. The process according to claim 5, wherein the cultivation step comprises two or more steps.

17. The process according to claim 16, wherein the culture medium in the steps later than the first step contains no nitrogen source.

18. The process according to claim 16, wherein the cultivation step comprises the steps of:

(1-1) cultivating the microorganism in a culture medium that contains polypeptone and at least one compound represented by the chemical formula (5); and (1-2) further cultivating the microorganism from the step 1-1 in a culture medium containing the compound represented by the chemical formula (5) and an organic acid or a salt thereof.

19. The process according to claim 18, wherein the organic acid or a salt thereof is one or more compounds selected from the group consisting of pyruvic acid, malic acid, lactic acid, citric acid, succinic acid and salts thereof.

20. The process according to claim 16, wherein the cultivation step comprises the steps of:

(1-3) cultivating the microorganism in a culture medium that contains a saccharide and at least one compound represented by the chemical formula (5); and (1-4) further cultivating the microorganism from the step 1-3 in a culture medium containing the compound represented by the chemical formula (5) and a saccharide.

21. The process according to claim 20, wherein the saccharide is one or more compounds selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose, and lactose.

22. The process according to claim 5, wherein the compound represented by the chemical formula (5) is 5-[4-(methylsulfanyl)phenoxy]valeric acid represented by the following chemical formula (6):

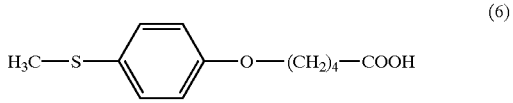

and the unit is represented by the following chemical formula (4):

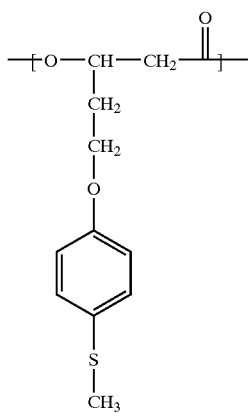

(4)

23. The process according to claim 5, further comprising the step of isolating the polyhydroxyalkanoate from cells of the microorganism cultivated in the cultivation step.

24. The process according to claim 23, wherein the step of isolating the polyhydroxyalkanoate comprises the step of treating with a solvent to solubilize and extract the polyhydroxyalkanoate accumulated in the cells of the microorganism cultivated in the cultivation step.

25. The process according to claim 24, wherein the solvent is one or more solvents selected from the group consisting of chloroform, dichloromethane, dioxane, tetrahydrofuran, acetonitrile, and acetone.

26. The process according to claim 23, wherein the step of isolating the polyhydroxyalkanoate comprises the step of disrupting cells of the microorganism.

27. The process according to claim 26, wherein the cells are disrupted by ultrasonic disruption, homogenization, pressure disruption, disruption with glass beads, trituration, grinding or freeze-thawing.

28. The process according to claim 5, wherein the microorganism belongs to genus *Pseudomonas*.

29. The process according to claim 28, wherein the microorganism that belongs to genus *Pseudomonas* is selected from the group consisting of *Pseudomonas cichorii* YN2 (FERM BP-7375), *Pseudomonas cichorii* H45 (FERM PB-7374), and *Pseudomonas jessenii* P161 (FERM BP-7376).

* * * * *

UNITED STATES PATENT AND TRADEMARK OFFICE
CERTIFICATE OF CORRECTION

PATENT NO. : 6,869,782 B2
DATED : March 22, 2005
INVENTOR(S) : Takashi Kenmoku et al.

It is certified that error appears in the above-identified patent and that said Letters Patent is hereby corrected as shown below:

Title page,
Item [56], References Cited, OTHER PUBLICATIONS,
"Y.B. Kim et al.," reference, "Obtain d" should read -- Obtained --.

Column 3,
Line 20, "different" should read -- different from --.

Column 4,
Lines 50 and 67, "different" should read -- different from --.

Column 5,
Line 46, "Pseudomonas" should read -- *Pseudomonas* --; and
Line 53, "was first" should read -- were first --.

Column 19,
Lines 50 and 67, "each" should read -- from each --.

Column 21,
Lines 19 and 36, "each" should read -- from each --.

Signed and Sealed this

Fourteenth Day of February, 2006

JON W. DUDAS
*Director of the United States Patent and Trademark Office*